US006482839B1

(12) United States Patent
Thornfeldt

(10) Patent No.: US 6,482,839 B1
(45) Date of Patent: Nov. 19, 2002

(54) PYRIDINE-THIOLS FOR TREATMENT OF A FOLLICULAR DERMATOSIS

(75) Inventor: Carl R. Thornfeldt, Nampa, ID (US)

(73) Assignee: Cellegy Pharmaceuticals, Inc., Foster City, CA (US)

( * ) Notice: Subject to any disclaimer, the term of this patent is extended or adjusted under 35 U.S.C. 154(b) by 0 days.

(21) Appl. No.: 09/145,822

(22) Filed: Sep. 2, 1998

Related U.S. Application Data

(63) Continuation-in-part of application No. PCT/US98/11270, filed on Jun. 2, 1998, and a continuation-in-part of application No. 09/089,302, filed on Jun. 1, 1998.
(60) Provisional application No. 60/047,360, filed on Jun. 2, 1997, provisional application No. 60/056,282, filed on Sep. 3, 1997, provisional application No. 60/058,752, filed on Sep. 12, 1997, and provisional application No. 60/056,290, filed on Sep. 3, 1997.

(51) Int. Cl.[7] ................. A61K 31/4402; A61P 17/00; A61P 17/10
(52) U.S. Cl. .......................... 514/345; 514/859
(58) Field of Search ................. 514/354, 859, 514/345

(56) References Cited

U.S. PATENT DOCUMENTS

| 4,307,089 A | 12/1981 | Melloh et al. ........... 424/245 |
| 5,284,649 A | 2/1994 | Juneja ..................... 424/67 |
| 5,686,489 A | 11/1997 | Yu et al. .................. 514/557 |

OTHER PUBLICATIONS

CA 119:233716, Martin et al., Jul., 1993.*
CA 99:10733, FDA Monograph, Dec., 1982.*
A. Bernard Ackerman, Histologic Diagnosis of Inflammatory Skin Diseases, *Library of Congress Cataloging in Publicatin Data*, pp. 640–663, 668–672 (1995).
T. Sakamoto et al., "Shampoos containing vitamin E Acetate and Dandruff–Controlling Agents," *chemical Abstracts* (Oct. 24, 1986) 106, Abstract 106:55622.

* cited by examiner

*Primary Examiner*—Edward J. Webman
(74) *Attorney, Agent, or Firm*—Townsend and Townsend and Crew, LLP

(57) ABSTRACT

This invention provides compositions and methods for treatment of skin and mucous membranes suffering from a follicular dermatosis. The compositions include one or more pyridine-thiols and tautomers with attached metallic moieties. Administration of the compounds to aging skin and mucous membranes in topical formulations, either as the only active ingredient or in combination with other known active ingredients to treat a follicular dermatosis. Additional compositions for treating follicular dermatosis contain one or more sulfides and oxides of these same metallic ions, either alone or in combination with other molecules. Topical formulations containing both a pyridine-thiol and tautomers with attached metallic moiety and a metallic sulfide and/or metallic oxide effectively treat skin and mucous membranes suffering from a follicular dermatosis.

16 Claims, No Drawings

PYRIDINE-THIOLS FOR TREATMENT OF A FOLLICULAR DERMATOSIS

CROSS-REFERENCE TO RELATED APPLICATIONS

This application is a continuation-in-part of PCT Patent Application No. PCT/US98/11270, which designates the United States and was filed Jun. 2, 1998, and of U.S. patent application Ser. No. 09/089,302, filed Jun. 1, 1998, both of which applications claim benefit of U.S. Provisional Patent Application Serial No. 60/047,360, filed Jun. 2, 1997, and No. 60/056,282, filed Sep. 3, 1997. This application also claims benefit of U.S. Provisional Patent Application Serial No. 60/058,752, filed Sep. 12, 1997 and No. 60/056,290, filed Sep. 3, 1997. Each of these applications is incorporated herein by reference for all purposes.

BACKGROUND OF THE INVENTION

1. Field of the Invention

This invention pertains to the field of treating and preventing signs and symptoms of aging, acneiform follicular diseases, mucocutaneous diseases, and neoplasia.

2. Background

Therapeutic products comprising metallic moieties have been used for many years for a variety of skin diseases. These medications have continued to be used to treat one or several skin diseases. For example, zinc pyrithione (zinc pyridine-2-thiol-1-oxide) is a therapeutic molecule that is used as the active ingredient in the most widely distributed commercially available medicated shampoos for treatment of dandruff and seborrheic dermatitis. In the past year, this compound has been introduced by two companies in a topical leave-on product to treat scalp psoriasis. Zinc pyrithione has multiple mechanisms of action including antiproliferative, keratolytic, astringent, antibacterial and anti-yeast properties. Zinc undecylenate has also been used as an antifungal agent. Zinc oxide has also had a long history as a sunblock and skin protectant especially for the diaper area. Zinc lactate (0.15%) is one component of a prescription product which also comprises erythromycin (2%) in a topical therapy for acne vulgaris.

U.S. Pat. No. 4,307,089 discusses a formulation that contains zinc pyrithione and/or its tautomeric form combined with undecylenic acid and the use of the formulation to treat dandruff. U.S. Pat. No. 5,284,649 discusses the use of heavy metal salts of hydroxypyridine thiones and their tautomeric forms, including zinc, zirconium, cadmium, tin, magnesium, sodium, calcium, aluminum and potassium pyrithione, as human deodorants.

Zinc is an essential mineral for animal cell growth and regeneration due to its integral structural role in certain enzymes especially proteases including carboxypeptidase A. Furthermore, the deoxyribonucleic acid (DNA) contains zinc finger binding domains utilized in transcription thus regulating gene activity. This element also functions as an enzyme activator, a coenzyme, and an antioxidant. Zinc and other bivalent ions including cobalt, copper, nickel, and manganese inhibit the binding of triiodothyronine to its nuclear receptor. Zinc, selenium, vanadium, and chromium all have documented insulin mimetic activity.

Selenium is a known antioxidant utilized as an immune modulator in naturpathic and lay medicine. Its major mechanism of action is via covalent binding to the key detoxification/antioxidant enzyme glutathione peroxidase. Multiple selenium sulfide shampoos have been on the prescription and over-the-counter markets for years to treat dandruff and seborrheic dermatitis. The difference between the two markets is that the prescription product has a much higher concentration of the selenium sulfide. These products are generally considered to be more effective than zinc pyrithione because of documented superior anti-microbial activity.

A topical product for wound healing, hair growth and to firm and improve elasticity of skin utilizes copper bound to a three amino acid peptide. Strontium has been reported to treat stinging/burning due to neurogenic inflammation but can be associated with bone deposition and marrow suppression. Multiple enzymes are known to require metallic ions as cofactors or are needed as catalysts. Several other metals currently are or have been in the past used a human disease medicines. Arsenic was a major topical treatment for psoriasis prior to the advent of corticosteroids. Gallium formulations injected intravenously are used in human medical diagnostic tests. Copper and silver salts are the active ingredients in topical products for cleansing and deodorizing stomas and burns.

Use of these metallic compounds as therapeutic compounds would be expected to have serious drawbacks because several, including nickel, chromium, and cobalt, are potent contact sensitizers of the skin and mucous membranes. Iron is a potent oxidant inducing cell damage. Bromine often induces a characteristic dermatosis known as bromoderma. High calcium levels in the stratum corneum inhibit normal barrier formation and desquamation.

Chronologically aged (intrinsic aging) mucocutaneous surfaces show a slight atrophy of the epidermis with straightening of the rete pegs thus weakening the dermal/epidermal junction measured by a decrease in the threshold for suction bullae. There is a moderate decrease in the number of Langerhans cells. Dryness of the skin is a common phenomenon. In the dermis there is lower cellularity and a decrease in elastic fibers and thus in skin elasticity. Capillaries are also fragile as evidenced by bruisability. Collagen metabolism is slower, and there is a progressive lowering in concentration of glycosaminoglycans. Wrinkling occurs, but it tends to be in the form of fine wrinkles that disappear temporarily with stretching. There is a decreased ability to mount inflammatory response and an increase in the time of healing after injury.

Photoaging induces deep wrinkles not erased by stretching, pigmentary alterations with areas of hyper- and hypopigmentation (actinic lentigines and leukodermas), and a variety of benign, premalignant, and malignant neoplasms. The dermis shows evidence of chronic inflammation with increased cellularity and enlarged fibroblasts. Elastotic degeneration occurs in which parts of the upper dermis is occupied by a basophilic fibrous material separating the dermis from the epidermis. This "grenz" zone is interpreted as a repair area. Glycosaminoglycan concentrations are increased, while elastin concentration is increased and arranged in atypical clumps. Collagen fibers are fragmented.

Psoriasis is the most commonly occurring papulosquamous disease of the skin and mucous membranes. It is a multi-factorial condition with epidermal hyperproliferation, scaling and marked epidermal and dermal inflammation. The lesions predominantly occur on knees, elbows, scalp, genitalia and buttocks. These plaques are characterized by sharply demarcated erythema with thick, white, micaceous scale. The majority of patients will be infected with a variety of micro-organisms, most commonly *Staphylococcus aureus,* although beta-hemolytic Streptococcus has been known to induce guttate psoriasis. This disease may occur at all age groups, last a lifetime and involve localized to wide-spread areas of the body. Other diseases within this papulosquamous group include among others lichen planus, pityriasis rubra pilaris, pityriasis rosea and other pityriases. Psoriasis is reportedly treated effectively with topical products containing only zinc pyrithione and zinc pyrithione with clobetasol, a corticosteroid.

Eczematous dermatitis is characterized by poorly demarcated, erythematous, scaly, vesicular, weeping, fissured, crusted patches associated with severe itching. Atopic, seborrheic and nummular dermatitis are the most common types. The lesions of atopic dermatitis occur on the face, neck and flexural surfaces. Patients suffering from eczematous dermatitis are usually also heavily infected with *Staphylococcus aureus* and less frequently with *Streptococcus pyogenes*.

Seborrheic dermatitis may mimic mild psoriasis. These lesions appear as erythematous patches with yellowish, greasy scales. Classic sites of involvement include scalp, eyebrows, paranasal chin folds, glabella, ears, presternal and interscapular areas of the trunk. Dandruff is a localized, mild form of this disease. Rarely, the seborrheic dermatitis may involve the entire body producing an exfoliative erythroderma. *Pityrosporum ovale* yeast has been shown to occur in at least 75% of patients afflicted with this disease. These eczematous diseases are treated with topical and systemic corticosteroids, antipruritics, antibiotics, tar, immunosupressives and psoralens plus ultraviolet A light and ultraviolet B light with varying degrees of success.

Ichthyoses are a group of chronic, scaling conditions that are divided into two large groups-the non-inflammatory retention hyperkeratotic diseases and the inflammatory hyperproliferative hyperkeratotic diseases. The latter group includes ten subtypes such as congenital ichthyosiform erythroderma, lamellar ichthyosis and epidermolytic hyperkeratosis. The two retention hyperkeratotic diseases include ichthyosis vulgaris and x-linked ichthyosis. These disfiguring ichthyotic diseases respond only moderately to systemic and topical retinoids, alpha hydroxy acids and greases. Certain sub-types of all of these epithelial diseases listed above may afflict the mucous membrane, but most lesions are on the skin.

Acne vulgaris is a multifactorial disease occurring in teenagers and young adults, with inflammatory and noninflammatory comedos on the face and upper trunk. The disease prerequisite is sebaceous gland dysfunction activated by androgens. For some reason as yet unknown, hypercornification in the gland orifice occurs blocking normal mobility of skin and follicle microorganisms. The restricted environment stimulates release of lipases by *Propionobacterium acnes* (an anaerobic corynebacterium). *Staphylococcus epidermidis* or *S. aureus,* certain gram negative bacteria, and *Pitrosporum ovale* (a yeast) may also be opportunistic organisms infecting up to 35% of patients with acne vulgaris. Damage to the gland structure and surrounding tissue by the lipases results in inflammatory papules, pustules and cysts. The comedos are free of pathogenic microbes. In some, the disease is only manifest as these noninflammatory lesions but all patients with inflammatory lesions have some comedos. Major treatments consist of oral and topical antibiotics and retinoids, topical salicylic acid and other hydroxy acids, other keratolytics, and benzoyl peroxide administered topically, oral antiandrogens, higher estrogen birth control pills, and nonsteroidal antiinflammatory agents including sulfones.

Acne conglobata, hidradenitis suppurativa, and acne keloidalis nuchae are the three components of dissecting follicular triad which is characterized by sebaceous gland cysts, and abscesses, fistulas and scarring of the scalp, axilla, perineum, and crural folds induced by a combined multiorganism infection of the several pathogens listed above. These are difficult diseases to control and/or cure but prolonged use of systemic retinoids are curative in most patients if they can tolerate the myriad of adverse reactions, some of which may have life-long sequelae.

Rosacea is a chronic disease of the primarily area of the face characterized by a heightened vascular response. It begins as a prominent intermittent flushing/blushing which becomes permanent followed by telangectasias. Papules and pustules often occur but no comedos develop. It occurs most commonly in women over 30 years of age with type I or type II skin. Topical and systemic antibiotics and topical corticosteroids are commonly used for treatment coupled with dietary manipulation and sunlight protection but complete remissions are uncommon and recurrences are the rule even with temporary cessation of therapy. Current therapy consists of antiinflammatory broad spectrum antimicrobials administered topically or orally. Antioxidants are also beneficial.

Folliculitis is a pustular inflammatory disease induced by usually one but otherwise possibly multiple pathogenic microbes including *Staphylococcus aureus,* beta hemolytic Streptococcus, and *Pityrosporum ovale.* Current therapy consists of the appropriate antimicrobial administered, usually systemically, with a topical keratolytic and antimicrobial or keratolytic washes.

*Pseudofolliculitis barbae* afflicts 83% of black males as well as any male of any race who has naturally curly hair. This disease results from the curly hair puncturing the skin inducing an inflammatory foreign body reaction and becoming a portal for infection. The current therapy which is rather unsatisfactory has consisted of topical acne vulgaris therapy. The most effective treatment is allowing beard growth.

A need exists for methods and compositions that are effective in preventing and/or reversing signs and symptoms of aging and for treating acneiform follicular diseases, as well as inflammatory and scaly diseases. The present invention fulfills these and other needs.

SUMMARY OF THE INVENTION

The present invention provides methods and compositions for treating various skin and mucous membrane conditions, including signs and symptoms of aging, skin diseases, follicular dermatosis, papulosquamous or eczematous dermatitis, ichthyotic diseases, and the like. The compositions of the invention include as an active ingredient one or more metal ions associated with a pyridine thiol, or a tautomer of a pyridine thiol. Alternatively, or in addition to the pyridine thiol, the compositions can include a metal oxide or a metal sulfide as an active ingredient. In some embodiments, the compositions also include one or more additional compounds that are effective in treating the disorder or signs and symptoms of aging.

The methods of the invention involve treating the mucocutaneous conditions by topically applying to an affected area of the mucocutaneous tissue a therapeutically effective amount of a topical formulation such as are described herein. Typically, the topical formulation will contain one or more of a metal ion associated with a compound selected from the group consisting of a pyridine-thiol and a tautomer of a pyridine-thiol, and/or a metal oxide or metal sulfide.

Thus, in some embodiments, the invention provides compositions that can be used to treat or prevent signs and symptoms of aging. These topical formulations can contain (a) a metal ion associated with a compound selected from the group consisting of a pyridine-thiol and a tautomer of a pyridine-thiol; and (b) one or more compounds which are effective in treating symptoms of aging of mucocutaneous tissue. In other embodiments, the topical formulations contain (a) a metal cation and an anion selected from the group consisting of an oxide and a sulfide; and (b) one or more compounds which are effective in treating symptoms and signs of aging of mucocutaneous tissue.

The invention also provides methods for treating or preventing symptoms and signs of aging by topically applying to an affected area of the mucocutaneous tissue a therapeutically effective amount of a topical formulation containing: (a) a metal ion associated with a compound selected from the group consisting of a pyridine-thiol and a tautomer of a pyridine-thiol; and (b) a metal oxide or a metal sulfide.

Additional embodiments of the invention provide compositions and methods for treating inflammatory and/or scaly diseased skin, adnexal and mucous membranes. These compositions generally include one or more pyridine-thiols, or tautomeric forms thereof, that are attached to one or more metallic ions. In additional embodiments, the compositions include one or more oxides or sulfides of the metallic ions. These compounds can be present as the only active ingredient, or can be combined with one or more compounds selected from the group of other FDA-approved prescription and/or OTC-monographed, FDA-allowed non-prescription therapeutic compounds and/or excipients and/or nutrients and/or cosmeceuticals.

In some embodiments, one or more of the pyridine thiols with attached metallic ion are combined with one or more sulfides and oxides of the metallic ions in topical formulations that are useful for treating these epithelial diseases. Furthermore, these latter formulations can additionally comprise one or more compounds effective in treating the signs and symptoms of these diseases.

These embodiments do not include topical formulations that include zinc pyrithione or selenium sulfide as the only active ingredients for treatment of psoriasis, dandruff and seborrheic dermatitis or formulations that include zinc pyrithione and clobetasol as the only active ingredients for treating psoriasis.

DETAILED DESCRIPTION

DEFINITIONS

The term "therapeutically effective amount" or "effective amount" is used herein to denote any amount of a topical formulation which will cause a substantial improvement in a disease condition (such as a subsidence of a lesion, for example) when applied to the affected area. A single application can be sufficient, or the formulation can be applied repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

A "cosmeceutical" is a product, typically non-prescription, that is utilized in the cosmetic industry which produces measurable structural changes in the skin and mucous membranes.

DESCRIPTION OF THE PREFERRED EMBODIMENTS

The present invention provides methods and compositions that are useful for treating or preventing signs and symptoms of various conditions of mucocutaneous tissues. The compositions of the invention contain one or more active compounds that are metal ions complexed with either pyridine thiols or are metal sulfides or metal oxides. The compositions are typically applied to skin or mucous membranes to prevent or treat the aging symptoms, which can be a result of chronologic (intrinsic) aging or photoaging.

This invention also provides methods and compositions for treating signs and symptoms of various diseases. These diseases, which include papulosquamous and eczematous diseases and disorders of cornification, including ichthyoses, are successfully reversed by administering topical formulations comprising one or more pyridine-thiols with attached metallic ion combined with one or more known FDA-approved or -allowed therapeutic compounds for these diseases and/or one or more Cosmetic and Toiletry Association-allowed excipients and/or cosmeceutical compounds.

A. Therapeutic and Anti-Aging Compounds and Formulations

The compounds of the invention include pyridine-thiols, as well as tautomers of the pyridine thiols, that are associated with a metal ion. In other embodiments, the compounds of the invention are metal ions associated with a sulfide ion or an oxide ion. In still other embodiments, the formulations of the invention include combinations of the pyridine-thiol oxides and sulfides and tautomers thereof. The zinc pyrithione and selenium pyrithione combination are preferred. Furthermore, this invention includes metallic sulfides and metallic oxides in combination as well as with pyridine-thiol with attached metallic ion or its tautomers. Selenium sulfide with zinc pyrithione is preferred. Preferred non-metallic compounds are 1-hydroxy-pyridine-thiol and 2-hydroxy-pyridine-thiol with the oxides and sulfides most preferred. Examples of these most preferred species include zinc pyrithione and selenium pyrithione.

The metal ions that can be included in the compounds of the invention are, for example, zinc, zirconium, vanadium, titanium, tin, strontium, sodium, silver, scandium, potassium, nickel, manganese, magnesium, iron, germanium, gallium, copper, cobalt, chromium, calcium, cadmium, bromine, and arsenic. Zirconium, zinc, vanadium, titanium, strontium, sodium, silver, selenium, potassium, manganese, magnesium, gallium, copper, calcium, and arsenic are preferred. Zinc, strontium, silver, selenium and copper are most preferred.

1. Pyridine Thiols

In some embodiments, the formulations of the invention include pyridine-thiols and/or tautomers of the pyridine thiols. Examples of suitable pyridine thiols include, but are not limited to, zinc pyrithione, selenium pyrithione, silver pyrithione, and copper pyrithione. Zinc pyridine-2-thiol-1-oxide (pyrithione) is a preferred pyridine thiol. The formulations of the invention further include combinations of two or more of these pyridine-thiols, with zinc pyrithione and selenium pyrithione being a preferred combination.

These organometallic compounds typically exist as bis adducts. For example, in a preferred embodiment, the empirical formula is $C_{10}H_8N_2OS_2Zn$. The synthesis of bis (2-pyridylthio)zinc 1,1'dioxide (i.e., zinc pyridine-2-thiol-1-oxide) is outlined in British Patent No. 761,171 and U.S. Pat. Nos. 3,236,733 and 3,281,366 all of which are incorporated herein by reference.

2. Metal Sulfides and Oxides

The invention also provides formulations in which an oxide or a sulfide anion is combined with a metallic ion. These oxides and sulfides can also be present in a formulation that also includes one or more metal ions associated with pyridine thiols as described above. The sulfides and oxides of the metallic ions that have activity against the signs and symptoms of aging and other conditions of the mucocutaneous tissue include, for example, any combination of a sulfide or an oxide moiety associated with a metal as set forth above. Preferred examples of these metals that can be combined with the oxides and sulfides include, for example, zirconium, zinc, vanadium, titanium, sodium, silver, selenium, potassium, manganese, magnesium, gallium, copper, and arsenic. Zinc oxide, zinc sulfide, strontium oxide, strontium sulfide, silver oxide, silver sulfide, selenium oxide, selenium sulfide, copper oxide, and copper sulfide are most preferred. Particularly preferred compounds include selenium sulfide and zinc oxide.

3. Formulations for Specific Diseases and Conditions

The formulations of the invention are useful for treating and preventing a wide variety of conditions of the mucocutaneous tissues. Examples of suitable formulations for various conditions are described below.

a. Signs and Symptoms of Aging

The compositions of the invention are useful for treating and preventing signs and symptoms of aging, which includes chronologic aging as well as photoaging. Signs or symptoms of aging include, for example, wrinkling, irregular pigmentation, laxity, inelasticity, fragility, fine lines, roughness, poor wound healing, and neoplasia.

Preferred compositions for this application include topical formulations that contain about 0.001% to about 60% by weight pyridine thiol, pyridine thiol tautomer, metal sulfide, or metal oxide. Particularly preferred compositions are topical formulations that contain about 0.1% to about 5% by weight of zinc pyrithione, silver pyrithione, selenium pyrithione, or copper pyrithione. One example of a preferred topical formulation contains about 2.5% by weight zinc pyrithione.

Additional preferred compositions are topical formulations that contain from about 0.025% to about 20% by weight metal oxide or metal sulfide. Particularly preferred topical formulations contain from about 0.1% to about 5% by weight zinc oxide or selenium sulfide. One example of a preferred topical formulation contains about 0.2% by weight of selenium sulfide.

The compositions of the invention can also contain, in addition to one or more of the above compounds, one or more additional compounds that are effective in treating signs or symptoms of aging. These additional compounds include, for example, alpha-, beta-, gamma- and polyhydroxy and keto acids, tretinoin, isotretinoin, retinol, retinaldehyde, ascorbic acid, tocopherol, dicarboxylic acids, lactones of hydroxy acids, kojic acids, linoleic and other carboxylic acids, compounds with a phenol ring as the primary active structure, derivatives of phenol, chloroacetic acids, corticosteroids, nonsteroidal anti-inflammatory agents, sulfones, catechins and other antioxidants, amino acids and other minerals, and esters, amides, salts, analogs, aldehydes, isomers, and derivatives thereof. The additional compound is typically present in the topical formulation at a concentration of about 0.01% to about 99.9% by weight.

Other examples of additional compounds that can be present in the compositions of the invention include, but are not limited to, salicylic, benzilic, malic, citric, tartaric, tropic, glucuronic, mandelic, benzoic, acetic, formic, fumaric, oxalic, propanoic, succinic, galactonic, galacturonic, glucoronic, glyceric, mucic, succharic, tartaronic, allolactic, phenyllactic, pyruvic, glycolic, lactic, linoleic, linolenic, azelaic, kojic, ascorbic, trichloroacetic, monochloroacetic, and dichloracetic, tetrahydroxypentanoic and hexahydroxyheptanoic acids, glucoconolactone, tocopherol, retinol, retinaldehyde, tretinoin, isotretinoin, vitamin D analogs, glucocorticosteroids, colchicine, dapsone, ibuprofen, ketoprofen, ketorolac, piroxicam, indomethacin, serine, alanine, glycine, phenol, arginine, thymol, menthol, eucalyptol, resorcinol, methyl resorcinol, hexyl resorcinol, 3-hydroxy butyric acid, 4-hydroxyvaleric acid, epigallocatechingallate, and esters, ethers, amides, analogs, derivatives, aldehydes, isomers and salts thereof. These compounds are typically present in the topical formulation at a concentration of about 0.5% to about 30% by weight.

b. Follicular Dermatoses

The compositions of the invention are also useful for treating skin and mucous membranes that are suffering from a follicular dermatosis. These compositions contain a therapeutically effective amount of one or more pyridine thiols, or tautomeric forms thereof, to which is attached one or more metallic ions, including those described above. The compositions can also include, in place of or in addition to the pyridine thiol, one or more metallic ions that are attached to an anion. Preferred anions include oxide and sulfide ions.

For example, these compositions can include a therapeutically effective amount of a dermatologic/cosmeceutical formulation that contains from about 0.01% to about 30.0% by weight of one or more active ingredients such as a) a compound that comprises a hydroxypyridine thione, or a tautomeric form thereof, attached to one or more metallic ions; and/or b) a metallic ion attached to an anion selected from the group consisting of an oxide and a sulfide. The metallic ions that are suitable for use in the formulations include, for example, zinc, zirconium, vanadium, titanium, tin, silver, scandium, sodium, selenium, potassium, nickel, magnesium, manganese, iron, gallium, germanium, copper, cadmium, calcium, chromium, cobalt, bromine, arsenic, and aluminum.

Examples of preferred dermatologic/cosmeceutical formulations contain from about 0.15% to about 4.0% by weight of a compound that includes a heavy metal (e.g., zinc, zirconium, vanadium, titanium, silver, selenium, sodium, potassium, magnesium, manganese, copper, gallium, arsenic or aluminum) attached to a 1-hydroxypridine thione oxide, a 2-hydroxypridine thione oxide, a 1-hydroxypyridine thione sulfide, or a 2-hydroxypyridine thione sulfide.

In some embodiments, the invention provides compositions that are particularly useful for treating follicular dermatoses such as acne vulgaris, acne conglobata, acne keloidalis nuchae, acne necroticans miliaris disseminata, rosacea, hidradenitis suppurativa, folliculitis, and pseudofolliculitis barbae. Preferred compositions for this application contain a therapeutically effective amount of a dermatologic/cosmeceutical formulation that contains from about 0.05% to about 10.0% by weight of a compound that has one or more heavy metallic ions attached to a 1-hydroxypyridine-thiol or a 2-hydroxypyridine-thiol. Preferred metallic ions include, for example, zinc, zirconium, titanium, tin, sodium, selenium, scandium, silver, potassium, manganese, magnesium, gallium, germanium, copper, cadmium, bromine, arsenic and aluminum. Other preferred compositions include about 0.25% by weight of one or more of zinc pyrithione, zirconium pyrithione, titanium pyrithione, silver pyrithione, selenium pyrithione, copper pyrithione, and aluminum pyrithione.

The compositions of the invention for use in treating follicular dermatoses can also include one or more additional biologically active compounds which have activity in the skin or mucous membranes. These compounds include, for example, keratolytics, hydroxyacids, anti-inflammatory agents, antimicrobials, immunosuppressives, carboxylic and amino acids, phenolics, retinoids, antioxidants, minerals, vitamins and their lactones, analogs, isomers, salts, esters, amides and derivatives thereof. These additional biologically active compounds can include, for example, salicylic, malic, citric, tartaric, pyruvic, glycolic, lactic, kojic, and azelaic acids, gluconolactone, serine, undecylenic acid, resorcinol, thymol, menthol, phenol, eucalyptol, sulfur, clindamycin, erythromycin, griseofulvin, sulfacetamide, metronidizole, ciprofloxan, ofloxan, chloramphenicol, glucocorticoids, piroxicam, ketoprofen, ketorolac, indomethacin, ketoconazole, terbenafine, naftifine, cicloprix, benzoyl peroxide, bacitracin, mupirocin, polymixin, gramicidin, chloroxylenol, benzylkonium chloride, benzethonium chloride, tobramycin, gentamicin, minocycline, tetracycline, silver salts, copper complexes, tretinoin, isotretinoin, retinaldehyde, adapalene, tazorotene vitamins A, C, E and D and their lactones, analogs, esters, amides, isomers, salts, and derivatives thereof.

One example of a preferred formulation contains about 0.25% by weight zinc pyrithione, and about 2.0% by weight salicylic acid. Another example of a preferred formulation contains about 2.5% by weight selenium sulfide, and about 2.0% by weight salicylic acid.

c. Keratinizing Epithelial Diseases and Disorders

The compounds and formulations of the invention also include those that are useful for topical treatment of keratinizing epithelial diseases and disorders. These compositions typically include therapeutically effective amounts of an active ingredient which can be one or more pyridinethiols with an attached metallic ion, or one or more metallic oxides or metallic sulfides. The formulations can also include one or more additional compounds, such as prescription and over-the-counter therapeutic compounds, cosmeceutical compounds, and excipient compounds.

d. Papulosquamous, Eczematous, Ichthyotic and Inflammatory Adnexal Diseases

The compositions of the invention are also useful for the topical treatment of skin and mucous membranes suffering from a papulosquamous, eczematous, ichthyotic and inflammatory adnexal diseases. Such diseases include, but are not limited to, psoriasis, lichen planus, pityriasis rubra pilaris, pityriasis rosea and other pityriases, contact dermatitis, seborrheic dermatitis, atopic dermatitis, ichthyosis vulgaris, acquired ichthyosis, x-linked ichthyosis, congenital primary ichthyoses including lamellar ichthyosis, congenital ichthyosiform erythroderma, epidermolytic hyperkeratosis, severe xerosis, acne vulgaris, acne conglobata, acne keloidalis nuchae, acne necroticans milliaris disseminata, hidradenitis suppurativa, folliculitis, rosacea, and pseudofolliculitis barbae.

Preferred compositions for treating these diseases include dermatologic/cosmeceutical formulations that have from about 0.001% to about 99.999% by weight of an active ingredient such as (a) one or more compounds selected from the group consisting of 1-hydroxypyridine thiols and 2-hydroxypyridine thiols attached to a metallic ion, or (b) one or more compounds selected from the group consisting of metal oxides and sulfides. The metals in these formulations can be, for example, one or more of zirconium, zinc, vanadium, titanium, tin, sodium, silver, selenium, scandium, potassium, nickel, manganese, magnesium, iron, germanium, gallium, copper, cobalt, calcium, chromium, cadmium, bromine, arsenic, and aluminum.

Preferably, these compositions also include one or more additional compounds such as, for example, anti-inflammatory, antimicrobial, immunosuppressive, chemotherapeutic, antiproliferative, antioxidant, keratolytic, humectant, surfactant, emulsifier, and nutrient compounds, and lactones, esters, amides, isomers, analogs and derivatives thereof. Examples of therapeutic compounds that can be included in the compositions include therapeutic compounds such as dapsone, meselamine, sulfasalazine, sulfacetamide, colchicine, calcipotriene, calcipitriol, ketoprofen, indomethacin, piroxicam, ketorolac, triamcinolone, flurandrenolide, prednicarbate, halcinonide, alclometasone, hydocortisone, desonide, amcinonide, fluocinonide, diflorasone, betamethasone, dexamethasone, desoximetasone, fluticasone, mometisone, fluocinolone, cyclosporin, rapamycin, tacrolimus, erythromycin, clindamycin, lincomycin, vancomycin, ciprofloxacin, ofloxacin, norfloxacin, doxycycline, meclomycin, tetracycline, minocycline, methotrexate, mercaptopurine, hydroxyurea, azathioprine, bleomycin, nitrogen mustard, carmustine, anthralin, tretinoin, etretinate, acitretin, isotretinoin, adapalene, tazarotene, metronidazole, terbenifine, ketoconazole, oxiconazole, sulconozole, fluconazole, itraconazole, griseofulvin, cicloprix, clotrimizole, econazole, miconazole, azelaic acid, benzoyl peroxide, gramicidin, bacitracin, polymixin, nystatin, tobramycin, gentamicin, chloramphenicol, amphotericin, dicloxacillin, carbenicillin, amoxicillin, cephalexin, cefixime, cefuroxime, cephadroxil, mupirocin, resorcinol, salicylic acid, sulfur, glycols, alcohols, carboxylic acids, sulfoxides, hydroxy acids, keto acids, terpenes, vitamins A, C, E, D, and the analogs, amides, isomers, derivatives, esters and salts thereof.

Preferred compositions include those having about 0.05 to 10.0% by weight of one or more of selenium sulfide, zinc oxide and titanium dioxide, along with an additional therapeutic compound. One example of a preferred composition for these applications contains about 0.25% by weight of selenium sulfide, and about 0.05% by weight of diflorasone acetate. Another example of a preferred composition contains about 2.5% by weight of selenium sulfide, and about 2.0% by weight of salicylic acid.

For treatment of diseases such as psoriasis, lichen planus, atopic dermatitis, seborrheic dermatitis and ichthyoses, preferred dermatologic/cosmeceutical formulations contain from about 0.05% to about 10.0% by weight of a compound selected from the group consisting of zirconium pyrithione, zinc pyrithione, titanium pyrithione, selenium pyrithione, sodium pyrithione, potassium pyrithione, magnesium pyrithione, gallium pyrithione, copper pyrithione and aluminum pyrithione; and an additional therapeutic compound. One example of a preferred formulation contains about 0.25% by weight of zinc pyrithione and/or selenium pyrithione; and about 2.0% by weight of salicylic acid. Another example of a preferred formulation contains about 0.25% by weight of zinc pyrithione and/or selenium pyrithione and about 1.0% by weight of clindamycin phosphate.

4. Formulations and Dosages

Typically, the compositions described herein will be in the form of a topical formulation for delivering the active ingredient. The formulation will typically contain the anti-aging compound in concentrations that range from about 0.001% to about 60.0% by weight, with about 0.025% to about 20.0% by weight preferred, and about 0.1% to about 5.0% by weight the most preferred. The formulations generally also include a non-toxic, pharmaceutically and/or cosmeceutically acceptable carrier. See, e.g., DRUG: FACTS AND COMPARISONS, Published by Facts and Comparisons, A Wolters Kluwer Company (1997) and Dermatological Formulations: Percutaneous Absorption, Barry (ed.), Marcel Dekker Inc. (1983).

The local absorption and efficacy of the compounds can be further enhanced by incorporating an appropriate amount of an excipient which can allow increased penetration of, or assist in the delivery of therapeutic molecules across, the stratum corneum permeability barrier of the skin. Many of these penetration enhancing molecules are known to those trained in the art of topical formulation. Examples include humectants such as urea and glycols such as propylene glycol, alcohols including ethanol, fatty acids such as oleic acid, surfactants such as isopropyl myristate and sodium lauryl sulfate, pyrrolidones, glycerol monolaurate, sulfoxides, terpenes including menthol, amines, amides, alkanes, alkanols, Orgelase and water. Vegetable oils or botanical oils containing high unsaturated fatty acids, e.g. safflower oil, olive oil, avocado oil, wheat germ oil, etc. or other chemicals can also facilitate absorption and delivery of compounds.

Pharmaceutically and cosmeceutically acceptable carriers will include water, saline, buffers, and other compounds described, e.g., in the Merck Index, Merck & Co., Rahway, N.J. See, also, Bioreversible Carriers in Drug Design, Theory and Application, Roche (ed.), Pergamon Press, (1987). Various considerations are described, e.g., in Gilman et al. (eds) (1990) Goodman and Gilman's: The Pharmacological Bases of Therapeutics, 8th Ed., Pergamon Press; Novel Drug Delivery Systems, 2nd Ed., Norris (ed.) Marcel Dekker Inc. (1989), and Remington's Pharmaceutical Sciences, the full disclosures of which are incorporated herein by reference. For standard dosages of conventional pharmacological agents, see, e.g., Physicians Desk Reference (1997 Edition); and American Medical Association (1997) Drug Evaluations (Subscriptions).

The compounds of the invention can be administered in a variety of forms. These include, for example, solid, semi-solid and liquid dosage forms, such as tablets, pills, powders, liquid solutions or suspensions, liposomes, nasal/aerosolized dosage forms, implants, injectable and infusible solutions. These agents can also be incorporated into various cosmetic and toiletry formulations (See, e.g., Flick E. W. Cosmetic and Toiletry Formulations, 2nd Ed., Noyes Publications, 1989). The preferred form depends on the intended mode of administration and therapeutic or cosmetic application.

Dosage forms for the topical administration of the compositions of the invention include various mixtures and combinations that can be applied topically and will permit even spreading and absorption into the cutaneous and mucosal surfaces. Examples include sprays, mists, aerosols, lotions, creams, solutions, gels, ointments, pastes, unguents, emulsions and suspensions. The active compound can be mixed under sterile conditions with a cosmeceutically or pharmaceutically acceptable carrier, and with any preservatives, buffers, or propellants which may be required. Topical preparations can be prepared by combining the active compounds with conventional pharmaceutical and/or cosmeceutical diluents and carriers commonly used in topical dry, liquid, cream and aerosol formulations. Ointment and creams can, for example, be formulated with an aqueous or oily base with the addition of suitable thickening and/or gelling agents. Such bases can include water and/or an oil such as liquid paraffin or a vegetable oil such as peanut oil or castor oil. Thickening agents which can be used according to the nature of the base include soft paraffin, aluminum stearate, cetostearyl alcohol, propylene glycol, polyethylene glycols, woolfat, hydrogenated lanolin, beeswax, and the like. Lotions can be formulated with an aqueous or oily base and will, in general, also include one or more of the following: stabilizing agents, emulsifying agents, dispersing agents, suspending agents, thickening agents, coloring agents, perfumes, and the like. Powders can be formed with the aid of any suitable powder base, e.g., talc, lactose, starch, and the like. Drops can be formulated with an aqueous base or non-aqueous base, and can also include one or more dispersing agents, suspending agents, solubilizing agents, and the like.

The ointments, pastes, creams and gels also can contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays also can contain excipients such as lactose, talc, silicic acid, aluminum hydroxide, calcium silicates and polyamide powder, or mixtures of these substances. Solutions of active compound can be converted into aerosols or sprays by any of the known means routinely used for making aerosol inhalant pharmaceuticals. In general, such methods comprise pressurizing or providing a means of pressurizing a container of the solution, usually with an inert carrier gas, and passing the pressurized gas through a small orifice. Sprays can additionally contain customary propellants, such as chlorofluorohydrocarbons and volatile unsubstituted hydrocarbons, such as butane and propane.

Multiple inactive ingredients are generally incorporated in topical formulations to improve cosmetic acceptability, and are optional ingredients in the formulations of this invention. Examples of ingredients are emulsifiers, humectants, surfactants, preservatives, fragrances, coloring agents, emollients, and fillers.

The topical pharmaceutical compositions can also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents.

One example of a topical formulation contains, in addition to the active agent, light mineral oil, sorbitol solution, hydroxyoctacosanyl hydroxystearate, methoxy PEG-22/dodecyl glycol copolymer, stearoxytrimethylsilane and stearic alcohol, dimethicone 50 cs, fragrance, methylparaben, edetate disodium, quarterium-15, butylates hydroxytoluene, citric acid (monohydrate) and purified water.

The dosage of a specific active compound of the invention depends upon many factors that are well known to those skilled in the art, for example, the particular compound; the condition being treated; the age, weight, and clinical condition of the recipient patient; and the experience and judgment of the clinician or practitioner administering the therapy. An effective amount of the compound is that which provides either subjective relief of symptoms or an objectively identifiable improvement as noted by the clinician or other qualified observer. The dosing range varies with the compound used, the route of administration and the potency of the particular compound.

Because the active compounds of the invention are each effective alone, the compositions can be essentially free of other agents that are effective against symptoms on mucocutaneous membranes. In some embodiments, however, the compositions include additional agents that are known, reported, or suspected to display, a therapeutic or anti-aging activity. In the case of anti-aging compositions, such molecules include, for example, keratolytics such as hydroxy acids and their lactones, ketoacids, phenolics, amino acids, carboxylic acids, antioxidants, vitamins A, C, E, certain nutrients, metallic elements, anti-inflammatory agents, and the esters, amides, aldehydes, salts, analogs, isomers and derivatives thereof. Some examples of specific anti-aging active ingredients that can be additionally incorporated into formulations of this invention include, for example, alpha-, beta-, gamma- and poly-hydroxy and keto acids as well as tretinoin, retinol, retinaldehyde, ascorbic acid, tocopherol, dicarboxylic acids, lactones of hydroxy acids, kojic acids, other carboxylic acids, including linoleic, compounds with a phenol ring as the primary active structure, derivatives of phenol, chloroacetic acids, corticosteroids, nonsteroidal anti-inflammatory agents, sulfones, catechins and other antioxidants, amino acids and other minerals, and the esters, amides, salts, analogs, aldehydes, isomers, and derivatives thereof.

The excipients that can be used in the formulations of the invention are typically compounds whose inclusion is allowed by the Cosmetic, Toiletry and Fragrance Association and that increase penetration of or assist in the delivery of therapeutic molecules across the stratum corneum permeability barrier. There are many of these penetration enhancing molecules known to those trained in the art of topical formulations. Examples are humectants such as urea and glycols, including propylene glycol and polyethylene glycol, alcohols such as ethanol, fatty acids such as oleic and linoleic acids, alpha-hydroxy acids such as lactic acid and glycolic acids, surfactants such as isopropyl myristate and sodium lauryl sulfate, pyrollidones, glycerol monolaurate, oleyl alcohol, sulfoxides, terpenes, phenolics including menthol and resorcinol, amines, amino acids, alkanes, alkanols, water and Orgelase. Many of these compounds have recently been shown to produce a measurable anatomic and/or physiologic change, including anti-aging effects, in the keratinizing epithelia giving rise to the term "cosmeceuticals". This class of compounds includes alpha-, beta- and gamma-hydroxy acids, chloracetic acids, carboxylic acids, phenolics, vitamins A, C, and E, catechins and other antioxidants, amino acids, corticosteroids and nonsteroidal antiinflammatory agents and their lactones, esters, amides, salts, analogs, isomers, and derivatives thereof. The preferred cosmeceutical compounds incorporated into this invention include salicylic, epigallocatechin gallate, ancic, mandelic, benzoic, acetic, formic, fumaric, oxalic, mucic, propanoic, succinic, glyceric, linoleic, trichloroacetic, saccharic, tartaronic, galactonic, galacturonic, glucuronic, tetra-hydroxypentanoic and hexahydroxy heptanoic, malic, citric, tartaric, pyruvic, glycolic, lactic, linolenic, stearic, palmitic, myristic, oleic, azelaic and kojic acids, gluconolactone, resorcinol, hexylresorcinol, methylresorcinol, retinol, retinaldehyde, tocopherol, alanine, glycine, serine, arginine, thymol, phenol, 4-hydroxy valeric acid, menthol, eucalyptol, and trichloroacetic, bichloroacetic, and nochloroacetic acids. The nutrients include vitamins, minerals, fats, proteins, carbohydrates, water and oxygen. The proceeding list is for examples only and is not intended to be all inclusive of known cosmeceutical compounds.

The FDA approved prescription therapeutic compounds that can be included in the formulations of the invention for treating epithelial diseases such as those described herein include, for example: nonsteroidal antiinflammatory agents, immunosuppressives, corticosteroids, antimicrobials, chemotherapeutics, vitamin D analogs and retinoids. The preferred compounds include dapsone, meselamine, sulfasalazine, sulfacetamide, silver sulfadiazine, colchicine, calcipotriene, calcipitriol, ibuprofen, flubiprofen, ketoprofen, indomethacin, piroxicam, ketorolac, chloroquine, quinacrine, hydroxy-chloroquine, triamcinolone, flurandrenolide, prednicarbate, halcinonide, alclometasone, hydocortisone, desonide, amcinonide, fluocinonide, diflorasone, betamethasone, dexamethasone, desoximetasone, fluticasone, mometisone, fluocinolone, cyclosporin, ascomycin, rapamycin, tacrolimus, erythromycin, clindamycin, lincomycin, vancomycin, ciprofloxacin, ofloxacin, norfloxacin, doxycycline, meclomycin, tetracycline, minocycline, methotrexate, mercaptopurine, hydroxyurea, azathioprine, bleomycin, cyclophosphamide, 5-fluorouracil, cis-platinin, chlorambucil, nitrogen mustard, carmustine, doxorubicin, daonorubicin, anthralin, transretinoic acid, etretinate, acitretin, isotretinoin, adapalene, tazarotene, metronidazole, terbenifine, ketoconazole, oxiconazole, sulconozole, fluconazole, itraconazole, griseofulvin, cicloprix, clotrimizole, econazole, miconazole, azelaic acid, benzoyl peroxide, gramicidin, bacitracin, polymixin, nystatin, tobramycin, gentamicin, chloramphenicol, amphotericin, dicloxacillin, carbenicillin, ampicillin, amoxicillin, amoxicillin-clavulanate, cephalexin, cefixime, cefuroxime, cephadroxil, and mupirocin. The FDA over-the-counter monograph allowed therapeutic compounds for dandruff, psoriasis and seborrheic dermatitis include hydrocortisone, resorcinol, salicylic acid, and sulfur in addition to zinc pyrithione and selenium sulfide which are included in this invention. The preceding list of the approved prescription and OTC therapeutic compounds for epithelial diseases is for example only and is not intended to be all inclusive for the FDA-approved and FDA-monographed compounds.

The compounds of the invention which are effective in treating and/or preventing signs and symptoms of aging and epithelial diseases can also be used in conjunction with anti-inflammatory and other therapeutic agents. Examples of anti-inflammatory agents include, for example, concentrated inflammation modifiers as described in commonly assigned U.S. patent application Ser. No. 09/087,744, filed on May 29, 1998.

This invention does not include topical formulations that contain zinc pyrithione or selenium sulfide as the only active ingredient to treat psoriasis, dandruff and seborrheic dermatitis, or zinc pyrithione and clobetasol to treat psoriasis.

B. Methods for Treating or Preventing Signs and Symptoms of Aging and Epithelial diseases The invention also provides methods for treating signs and symptoms of aging of the skin and mucosal membranes, as well as methods for treating epithelial diseases such as those described herein. The treatments involve administering an effective amount of a compound of the invention as described herein, typically as a topical formulation. The formulations of this invention are generally applied to the locally affected diseased or abnormal skin and/or mucous membranes. These formulations include various mixtures and combinations that can be applied topically and will permit even spreading and absorption into the cutaneous and mucosal surfaces. Examples include sprays, mists, aerosols, lotions, creams, solutions, gels, ointments, pastes, unguents, emulsions and suspensions.

To treat or prevent an aging-related condition of the skin or mucosal membrane, a composition that contains one or more of the compounds described herein is administered to the skin or mucosal membrane in an amount effective to modulate the condition. An effective amount can be determined by applying the compositions containing the compounds of the invention to test animal models.

The methods described herein find use in the treatment and/or prevention of a variety of signs and symptoms of aging. Such signs and symptoms against which the methods are effective include, but are not limited to, wrinkling, irregular pigmentation, laxity, inelasticity, fragility, roughness, poor wound healing, and neoplasia.

Also provided are methods for treating or preventing diseases such as acneiform follicular diseases, inflammation, and scaly diseases. These methods also involve topical application of an effective amount of the compounds and formulations of the invention to affected areas of the skin and/or mucocutaneous membranes. Again, an effective amount can be determined by applying the compositions to test animals and human subjects. It will also be readily apparent to those skilled in the art. The amount will vary with the condition being treated, the size, number and distribution of the lesions and the type and concentration of the formulation applied.

EXAMPLES

The following examples are offered to illustrate, but not to limit the present invention.

Example 1

Formulation A

A 0.25% zinc pyrithione lotion was produced by dissolving 2.5 mg of zinc-1-hydroxypyridine-2-thione (Sigma: St. Louis, Mo.) in 100 milliliters of 60% ethanol, 25% propylene glycol and 15% water. This emulsion was designed to be thoroughly shaken prior to topical application to affected mucocutaneous surface. Once applied, Formulation A was allowed to dry for 3 to 5 minutes; glycerin was then applied sparingly to cover the whole surface.

Example 2

Application

Three middle aged patients afflicted with mild acne vulgaris with about 10 inflammatory lesions on each side of the face and moderate fine wrinkling, irregular pigmentation, and loss of elasticity were treated with Formulation A twice daily for 12 weeks. All patients experienced complete clearing of the acne lesions and noticeable decrease in the degree and number of wrinkles and pigmentation with improvement in elasticity.

Example 3

Formulation B

Formulation A was adjusted to Formulation B by adding 5 mg of salicylic acid (Sigma: St. Louis, Mo.) by weight to make a 0.5% solution. Each application was performed as in Example 1 above.

Example 4

Application

Two middle aged patients were treated with Formulation B twice daily for 16 weeks. Both experienced a noticeable diminution of fine wrinkling, irregular pigmentation, and improved skin texture.

Example 5

Formulation C

Formulation C was prepared by dissolving 25 milligrams of selenium sulfide (Sigma: St. Louis, Mo.) in 100 milliliters of 60% ethanol, 25% propylene glycol, and 15% water to make a 2.5% by weight selenium sulfide solution. Each application was performed as in Example 1 above.

Example 6

Application

Two middle aged males suffered from skin aging experienced definite improvement in all signs with twice daily application of Formulation C for 16 weeks.

Example 7

Application

Three patients suffering from frequently recurrent facial seborrheic dermatitis and moderate signs of aging applied Formulation C twice daily for sixteen weeks. There was complete clearing of the dermatitis within four weeks, and no recurrences during the sixteen week period. All patients experienced improved texture, decreased roughness, and diminished fine wrinkles.

Example 8

Formulation D

A 0.25% zinc pyrithione lotion was produced by dissolving 2.5 mg of zinc-1-hydroxypyridine-2-thione (Sigma: St. Louis, Mo.) in 100 milliliters of 60% ethanol, 25% propylene glycol, and 15% water. This emulsion was to be thoroughly shaken prior to topical application to diseased skin.

Example 9

Application

Three teenage patients afflicted with acne vulgaris characterized by in excess of 20 inflammatory papules and pustules were treated with Formulation D twice daily for twelve weeks. All patients experienced significant but not complete clearing. The average improvement was 56% decrease in the number of inflammatory lesions and 45% decrease in comedos.

Example 10

Application

Two middle age patients afflicted with rosacea experienced marked improvement after nine weeks of using Formulation D twice daily to their face.

Example 11

Application

Two middle age men suffering from pseudofolliculitis barbae were treated with Formulation D for nine weeks. Both experienced >50% decrease in the number of inflammatory lesions.

Example 12

Application

Three adults afflicted with acne necroticans miliaris disseminata applied Formulation D twice daily for nine weeks. All observed >50% decrease in the number of tender lesions.

Example 13

Formulation E

Formulation E was produced by adding 20 mg of salicylic acid (Sigma: St. Louis, Mo.) to Formulation D to make a 2.0% by weight salicylic acid solution.

Example 14

Application

Two teenagers were treated with Formulation E twice daily for twelve weeks. Both experienced an average of 92% clearing of inflammatory acne lesions.

Example 15

Formulation F

Formulation F was prepared by dissolving 25 milligrams of selenium sulfide (Sigma: St. Louis, Mo.) in 100 milliliters of 60% ethanol, 25% propylene glycol, and 15% water to make a 2.5% by weight selenium sulfide solution.

Example 16

Application

Two middle aged males suffering from recurrent pityresporum folliculitis experienced complete clearing with twice daily application of Formulation F for 23 and 26 days respectively.

Example 17

Formulation G

A 0.25% zinc pyrithione lotion was produced by dissolving 25 mg. of zinc pyrithione (Sigma; Milwaukee, Wis.) in 60% ethanol, 25% propylene glycol and 15% water. 2% salicylic acid by weight was added. This emulsion was thoroughly shaken prior to topical application to the affected mucocutaneous surface. Once applied it was allowed to dry for up to five minutes followed by application of glycerin.

Example 18

Application

Three patients suffering with psoriasis were treated with Formulation G twice daily for six weeks. Two patients experienced complete clearing of the lesions and one improved by over 50%, according to a standard grading scale.

Example 19

Application

Two patients suffering from facial seborrheic dermatitis were treated with Formulation G twice daily. Both experienced complete clearing within two weeks of use.

Example 20

Application

Two patients suffering from x-linked ichthyosis were treated with formulation G twice daily. The lesions of both completely cleared within four weeks.

Example 21

Formulation H

This product was prepared by dissolving 25 mg of selenium pyrithione and 10 mg of clindamycin phosphate, (Sigma; Milwaukee, Wis.) in 100 mL of 60% ethanol, 25% propylene glycol, and 15% water to make a 2.5% by weight selenium pyrithione and 1.0% by weight clindamycin phosphate solution.

Example 22

Application

Two patients suffering with oral lichen planus resistant to other topical therapies experienced complete clearing of all lessons with twice daily application of formulation H for twelve weeks.

Example 23

Formulation I

Formulation I was prepared by dissolving 0.2% by weight (20 mg) selenium sulfide and 0.05% by weight (5 mg) diflorasone acetate (Sigma; Milwaukee, Wis.) in 100 mL of 60% ethanol, 25% propylene glycol and 15% water.

Example 24

Application

Three patients suffering from recurrent atopic dermatitis were treated with Formulation I twice daily. Complete clearing of the dermatitis was achieved within two weeks and no recurrences developed over the following four months.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for the treatment of skin and mucous membranes suffering from rosacea, folliculitis or pseudofolliculitis barbae, said method comprising applying to an affected area a therapeutically effective amount of an active ingredient selected from the group consisting of:
   (a) one or more pyridine-thiols, or tautomeric forms thereof, to which is attached a metallic ion; and
   (b) one or more members selected from the group consisting of sulfides and oxides attached to a metallic ion.

2. The method of claim 1, wherein said formulation is applied topically to skin or mucous membranes in a formulation selected from the group consisting of sprays, mists, aerosols, solutions, lotions, gels, creams, ointments, pastes, unguents, emulsions and suspensions.

3. The method of claim 1, wherein the method comprises applying to the affected area a therapeutically effective amount of a dermatologic/cosmeceutical formulation comprising from about 0.01% to about 30.0% by weight of an active ingredient selected from the group consisting of:
   (a) a compound that comprises a hydroxypyridine thione, or a tautomeric form thereof, attached to a metallic ion
   (b) a metallic ion attached to an anion selected from the group consisting of an oxide and a sulfide, wherein the metallic ion is selected from the group consisting of zinc, zirconium, vanadium, titanium, tin, silver, scandium, sodium, selenium, potassium, nickel, magnesium, manganese, iron, gallium, germanium, copper, cadmium, calcium, chromium, cobalt, bromine, arsenic and aluminum.

4. A method for the treatment of skin and mucous membranes suffering from rosacea, folliculitis or pseudofolliculitis barbae, said method comprising applying to an affected area a therapeutically effective amount of a dermatologic/cosmeceutical formulation, wherein said dermatologic/cosmeceutical formulation comprises from about 0.15% to about 4.0% by weight of a compound that comprises a heavy metal selected from the group of zinc, zirconium, vanadium, titanium, silver, selenium, sodium, potassium, magnesium, manganese, copper, gallium, arsenic and aluminum, wherein the heavy metal is attached to a moiety selected from the group of 1-hydroxy-2-pyridine thione and 2-pyridinethiol 1-oxide.

5. A method for the treatment of skin and mucous membranes suffering from rosacea, folliculitis or pseudofolliculitis barbae, said method comprising applying to an affected area a therapeutically effective amount of a formulation comprising:

(a) one or more members selected from the group consisting of sulfides and oxides attached to a metallic ion, and (b) one or more compounds that have dermatological activity in the skin and mucous membranes.

6. The method of claim 1, said method comprises applying to the affected area a therapeutically effective amount of a dermatologic/cosmeceutical formulation comprising from about 0.05% to about 10.0% by weight of a compound that comprises one or more heavy metallic ion selected from the group of zinc, zirconium, titanium, tin, sodium, selenium, scandium, silver, potassium, manganese, magnesium, gallium, germanium, copper, cadmium, bromine, arsenic and aluminum, attached to a moiety selected from the group consisting of 1-hydroxy-2-pyridine thione and 2-pyridinethiol 1-oxide.

7. The method of claim 6, wherein the formulation comprises about 0.25% by weight of a compound selected from the group consisting of zinc pyrithione, zirconium pyrithione, titanium pyrithione, silver pyrithione, selenium pyrithione, copper pyrithione, and aluminum pyrithione.

8. The method of claim 1, wherein said formulation comprises an additional dermatologically active compound selected from the group consisting of keratolytics, hydroxyacids, anti-inflammatory agents, antimicrobials, immunosuppressives, carboxylic and amino acids, phenolics, retinoids, antioxidants, minerals, vitamins and their lactones, analogs, isomers, salts, esters, amides and derivatives thereof.

9. The method of claim 8, wherein the additional dermatologically active compound is selected from the group consisting of: salicylic, malic, citric, tartaric, pyruvic, glycolic, lactic, kojic, and azelaic acids, gluconolactone, serine, undecylenic acid, resorcinol, thymol, menthol, phenol, eucalyptol, sulfur, clindamycin, erythromycin, griseofulvin, sulfacetamide, metronidizole, ciprofloxan, ofloxan, chloramphenicol, glucocorticoids, piroxicam, ketoprofen, ketorolac, indomethacin, ketoconazole, terbinafine, naftifine, cicloprix, benzoyl peroxide, bacitracin, mupirocin, polymixin, gramicidin, chloroxylenol, benzylkonium chloride, benzethonium chloride, tobramycin, gentamicin, minocycline, tetracycline, silver salts, copper complexes, tretinoin, isotretinoin, retinaldehyde, adapalene, tazorotene, vitamins A, C, E and D and their lactones, analogs, esters, amides, isomers, salts, and derivatives thereof.

10. The method of claim 4, wherein said formulation is applied topically to skin or mucous membranes in a formulation selected from the group consisting of sprays, mists, aerosols, solutions, lotions, gels, creams, ointments, pastes, unguents, emulsions and suspensions.

11. The method of claim 4, wherein the follicular dermatosis is selected from the group of rosacea, hidradenitis suppurativa, folliculitis, and pseudofolliculitis barbae.

12. The method of claim 4, wherein the formulation comprises about 0.25% by weight of a compound selected from the group consisting of zinc pyrithione, zirconium pyrithione, titanium pyrithione, silver pyrithione, selenium pyrithione, copper pyrithione, and aluminum pyrithione.

13. The method of claim 12, wherein said formulation comprises an additional dermatologically active compound selected from the group consisting of keratolytics, hydroxyacids, anti-inflammatory agents, antimicrobials, immunosuppressives, carboxylic and amino acids, phenolics, retinoids, antioxidants, minerals, vitamins and their lactones, analogs, isomers, salts, esters, amides and derivatives thereof.

14. The method of claim 5, wherein said formulation is applied topically to skin or mucous membranes in a formulation selected from the group consisting of sprays, mists, aerosols, solutions, lotions, gels, creams, ointments, pastes, unguents, emulsions and suspensions.

15. The method of claim 5, wherein the therapeutically effective amount of the formulation comprises from about 0.01% to about 30.0% by weight of the active ingredient.

16. The method of claim 5, wherein compound (b) is selected from the group consisting of keratolytics, hydroxyacids, anti-inflammatory agents, antimicrobials, immunosuppressives, carboxylic and amino acids, phenolics, retinoids, antioxidants, minerals, vitamins and their lactones, analogs, isomers, salts, esters, amides and derivatives thereof.

\* \* \* \* \*